US012381006B2

(12) United States Patent
Grady et al.

(10) Patent No.: US 12,381,006 B2
(45) Date of Patent: Aug. 5, 2025

(54) SYSTEMS AND METHODS TO PROCESS ELECTRONIC IMAGES TO IDENTIFY DIAGNOSTIC TESTS

(71) Applicant: PAIGE.AI, Inc., New York, NY (US)

(72) Inventors: Leo Grady, Darien, CT (US); Christopher Kanan, Pittsford, NY (US); Jorge Sergio Reis-Filho, New York, NY (US); Belma Dogdas, Ridgewood, NJ (US); Matthew Houliston, Boston, MA (US)

(73) Assignee: Paige.AI, Inc., New York, NY (US)

( * ) Notice: Subject to any disclaimer, the term of this patent is extended or adjusted under 35 U.S.C. 154(b) by 0 days.

(21) Appl. No.: 18/627,817

(22) Filed: Apr. 5, 2024

(65) Prior Publication Data

US 2024/0257977 A1     Aug. 1, 2024

Related U.S. Application Data

(63) Continuation of application No. 17/951,421, filed on Sep. 23, 2022, now Pat. No. 11,978,560, which is a
(Continued)

(51) Int. Cl.
*G16H 50/20*     (2018.01)
*G06F 18/214*    (2023.01)
(Continued)

(52) U.S. Cl.
CPC .......... *G16H 50/20* (2018.01); *G06F 18/214* (2023.01); *G06T 7/0012* (2013.01); *G06V 10/25* (2022.01);
(Continued)

(58) Field of Classification Search
CPC ........ G16H 10/20; G16H 10/40; G16H 30/40; G16H 50/20; G16H 50/30; G06F 18/214;
(Continued)

(56) References Cited

U.S. PATENT DOCUMENTS 10,282,588 B2     5/2019   Comaniciu et al.
2011/0301859 A1  12/2011   Carter et al.
(Continued)

FOREIGN PATENT DOCUMENTS

WO          2014130592 A1     8/2014

OTHER PUBLICATIONS

Mercan et al., "Assessment of Machine Learning of Breast Pathology Structures for Automated Differentiation of Breast Cancer and High-Risk Proliferative Lesions", JAMA Network Open, 2019, 2(8), pp. 1-11 (Year: 2019).

*Primary Examiner* — Ping Y Hsieh
*Assistant Examiner* — Jose M Torres
(74) *Attorney, Agent, or Firm* — Bookoff McAndrews, PLLC

(57) ABSTRACT

Systems and methods are disclosed for processing digital images to identify diagnostic tests, the method comprising receiving one or more digital images associated with a pathology specimen, determining a plurality of diagnostic tests, applying a machine learning system to the one or more digital images to identify any prerequisite conditions for each of the plurality of diagnostic tests to be applicable, the machine learning system having been trained by processing a plurality of training images, identifying, using the machine learning system, applicable diagnostic tests of the plurality of diagnostic tests based on the one or more digital images and the prerequisite conditions, and outputting the applicable diagnostic tests to a digital storage device and/or display.

20 Claims, 8 Drawing Sheets

Related U.S. Application Data continuation of application No. 17/519,834, filed on Nov. 5, 2021, now Pat. No. 11,488,719, which is a continuation of application No. 17/504,867, filed on Oct. 19, 2021, now Pat. No. 11,335,462.

(60) Provisional application No. 63/104,923, filed on Oct. 23, 2020.

(51) Int. Cl.
| | | |
|---|---|---|
| *G06T 7/00* | (2017.01) | |
| *G06V 10/25* | (2022.01) | |
| *G06V 30/19* | (2022.01) | |
| *G16H 10/20* | (2018.01) | |
| *G16H 30/40* | (2018.01) | |

(52) U.S. Cl.
CPC ....... *G06V 30/19147* (2022.01); *G16H 10/20* (2018.01); *G16H 30/40* (2018.01); *G06T 2207/20081* (2013.01); *G06T 2207/30004* (2013.01); *G06V 2201/03* (2022.01)

(58) Field of Classification Search
CPC ......... G06T 7/0012; G06T 2207/20081; G06T 2207/30004; G06V 10/25; G06V 10/70; G06V 20/698; G06V 30/19147; G06V 2201/03

See application file for complete search history.

(56) References Cited

U.S. PATENT DOCUMENTS

| | | |
|---|---|---|
| 2016/0314580 A1 | 10/2016 | Lloyd et al. |
| 2016/0321414 A1 | 11/2016 | Salganicoff et al. |
| 2018/0068083 A1 | 3/2018 | Cohen et al. |
| 2018/0315505 A1 | 11/2018 | Itu et al. |
| 2019/0130067 A1 | 5/2019 | Passerini et al. |
| 2020/0152326 A1 | 5/2020 | Sanchez-Martin et al. |
| 2020/0160032 A1 | 5/2020 | Allen et al. |
| 2020/0273581 A1* | 8/2020 | Wolf ..................... G16H 40/63 |
| 2020/0279126 A1 | 9/2020 | Nie et al. |
| 2020/0294231 A1 | 9/2020 | Tosun et al. |
| 2021/0233642 A1 | 7/2021 | Sue et al. |
| 2023/0005575 A1* | 1/2023 | Borgert .................. G16H 10/60 |
| 2024/0387048 A1* | 11/2024 | Habboushe ............ G16H 50/70 |

* cited by examiner

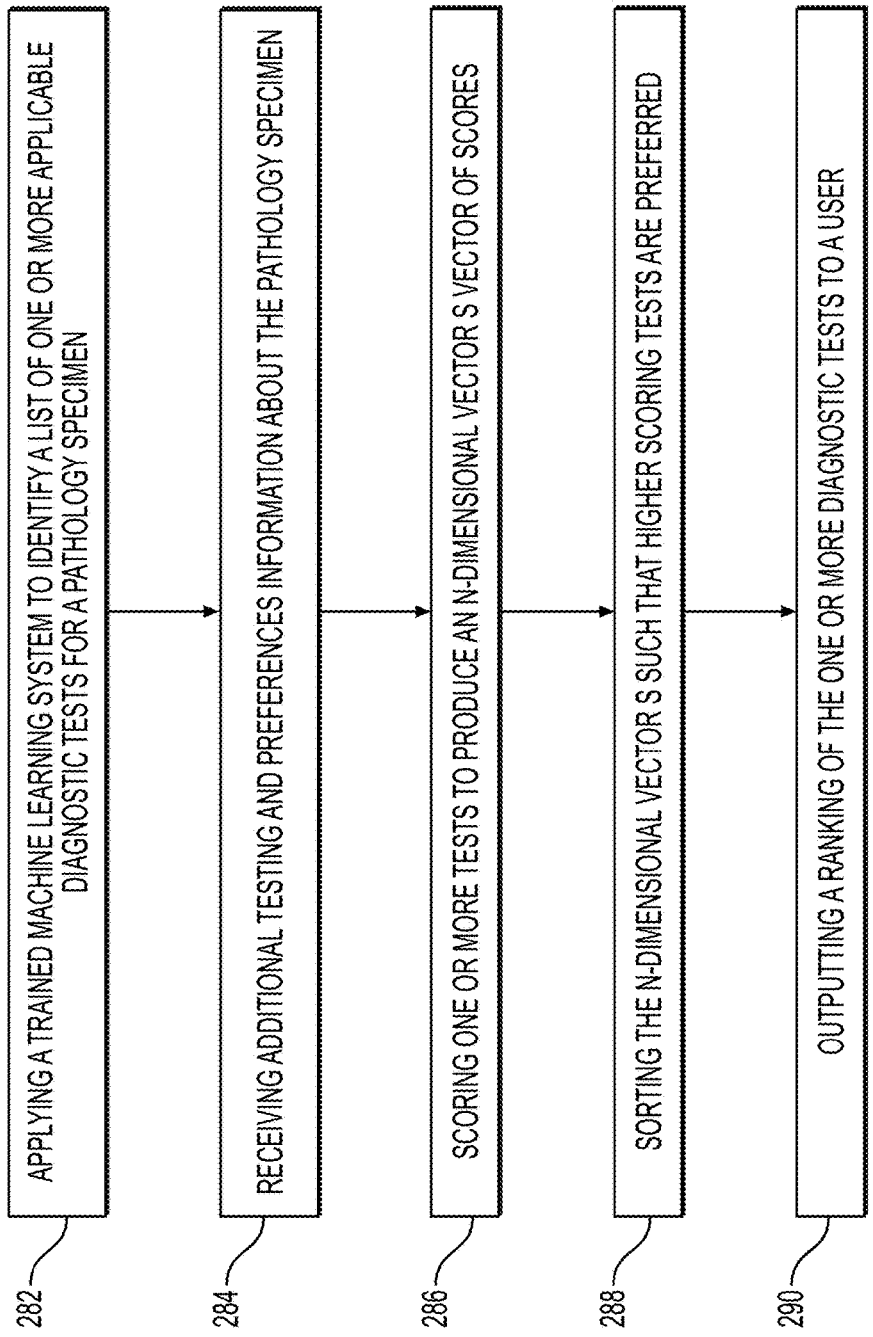

SYSTEMS AND METHODS TO PROCESS ELECTRONIC IMAGES TO IDENTIFY DIAGNOSTIC TESTS

RELATED APPLICATION(S)

This application is a continuation of U.S. application Ser. No. 17/951,421, filed on Sep. 23, 2022, which is a continuation of U.S. application Ser. No. 17/519,834 filed on Nov. 5, 2021, now U.S. Pat. No. 11,488,719, which is a continuation of U.S. application Ser. No. 17/504,867, filed Oct. 19, 2021, now U.S. Pat. No. 11,335,462, which claims priority to U.S. Provisional Application No. 63/104,923 filed Oct. 23, 2020, the entire disclosures of which are hereby incorporated herein by reference in their entireties.

FIELD OF THE DISCLOSURE

Various embodiments of the present disclosure pertain generally to image processing methods. More specifically, particular embodiments of the present disclosure relate to systems and methods for processing electronic images to prioritize and/or identify diagnostic tests.

BACKGROUND

Diagnostic testing methods for identifying therapies and courses of treatment for diseased tissues continue to be developed and made available for clinical practice. Diagnostic testing has the potential to benefit the patient by ruling out ineffective treatments and/or by identifying therapies that are most likely to provide significant benefit for treating a patient's disease via the detection of an absence and/or presence of a biomarker (e.g., a practice known as "precision medicine"). However, important diagnostic testing may not be done for a patient due to a variety of factors, including unfamiliarity of the doctor with testing, unavailability of testing within the facility, lack of viable sample to successfully execute the recommended tests, a low pre-test expectation that a specific test might yield positive results for this patient, or the high cost of the treatment that the test is identifying. Techniques presented herein may address this clinical need by identifying and prioritizing which tests might be beneficial for patients and making this information available to the patients and physicians.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing electronic images to recommend diagnostic tests based on a tissue specimen.

A method for processing digital images to identify diagnostic tests, the method comprising receiving one or more digital images associated with a pathology specimen, determining a plurality of diagnostic tests, applying a machine learning system to the one or more digital images to identify any prerequisite conditions for each of the plurality of diagnostic tests to be applicable, the machine learning system having been trained by processing a plurality of training images, identifying, using the machine learning system, applicable diagnostic tests of the plurality of diagnostic tests based on the one or more digital images and the prerequisite conditions, and outputting the applicable diagnostic tests to a digital storage device and/or display.

A system for processing digital images to identify diagnostic tests, the method comprising receiving one or more digital images associated with a pathology specimen, determining a plurality of diagnostic tests, applying a machine learning system to the one or more digital images to identify any prerequisite conditions for each of the plurality of diagnostic tests to be applicable, the machine learning system having been trained by processing a plurality of training images, identifying, using the machine learning system, applicable diagnostic tests of the plurality of diagnostic tests based on the one or more digital images and the prerequisite conditions, and outputting the applicable diagnostic tests to a digital storage device and/or display.

A non-transitory computer-readable medium storing instructions that, when executed by a processor, cause the processor to perform a method for processing digital images to identify diagnostic tests, the method comprising receiving one or more digital images associated with a pathology specimen, determining a plurality of diagnostic tests, applying a machine learning system to the one or more digital images to identify any prerequisite conditions for each of the plurality of diagnostic tests to be applicable, the machine learning system having been trained by processing a plurality of training images, identifying, using the machine learning system, applicable diagnostic tests of the plurality of diagnostic tests based on the one or more digital images and the prerequisite conditions, and outputting the applicable diagnostic tests to a digital storage device and/or display.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 2D is a flowchart illustrating an exemplary method for using the trained system to identify applicable tests for a pathology specimen, according to an exemplary embodiment of the present disclosure.

DESCRIPTION OF THE EMBODIMENTS

Figure 1A:
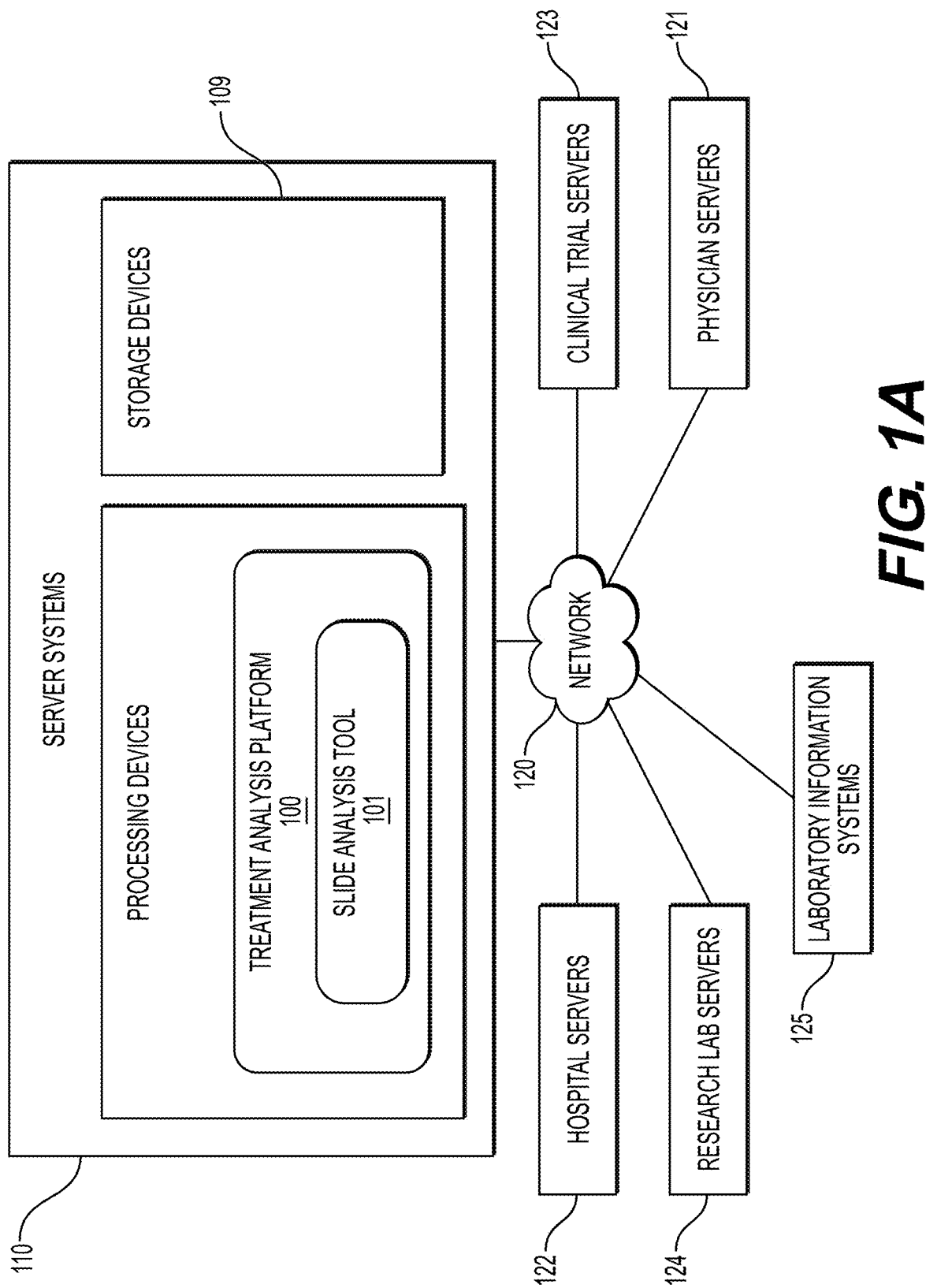
FIG. 1A illustrates an exemplary block diagram of a system and network for identifying diagnostic tests applicable for a pathology specimen, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Computational assays that use machine learning may in some cases determine the outcome of a diagnostic test directly, and in other cases they may be used to exclude or prioritize tests that are unlikely to be valuable and/or help prioritize between available tests. One or more embodiments of the present disclosure implement this functionality along with ranking non-excluded tests based on ancillary information such as their availability and cost.

While existing computational assays are focused on identifying a presence or absence of a disease/biomarker, techniques presented herein may include identifying the diagnostic tests that may better inform treatment while also identifying the tests that are unlikely to be informative for the clinician.

FIG. 1A illustrates an exemplary block diagram of a system and network for identifying diagnostic tests applicable for a pathology specimen, according to an exemplary embodiment of the present disclosure.

Specifically, FIG. 1A illustrates an electronic network 120 that may be that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers and/or handheld mobile devices. According to an exemplary embodiment of the present application, the electronic network 120 may also be connected to server systems 110, which may include processing devices that are configured to implement a treatment analysis platform 100, which includes a slide analysis tool 101 for determining specimen property or image property information pertaining to digital pathology image(s), and using machine learning to determine whether a disease or infectious agent is present, according to an exemplary embodiment of the present disclosure. The slide analysis tool 101 may also predict a suitable diagnostic test for a pathology specimen.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combinations thereof. The physician servers 121, hospital servers 122, clinical trial servers 123, research lab servers 124 and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124 and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities. For example, the processing devices may include a machine learning tool for a treatment analysis platform 100, according to one embodiment. Alternatively or in addition, the present disclosure (or portions of the systems and methods of the present disclosure) may be performed on a local processing device (e.g., a laptop).

The physician servers 121, hospital servers 122, clinical trial servers 123, research lab servers 124 and/or laboratory systems 125 refer to systems used by pathologists for reviewing the images of the slides. In hospital settings, tissue type information may be stored in a laboratory information system 125.

Figure 1B:
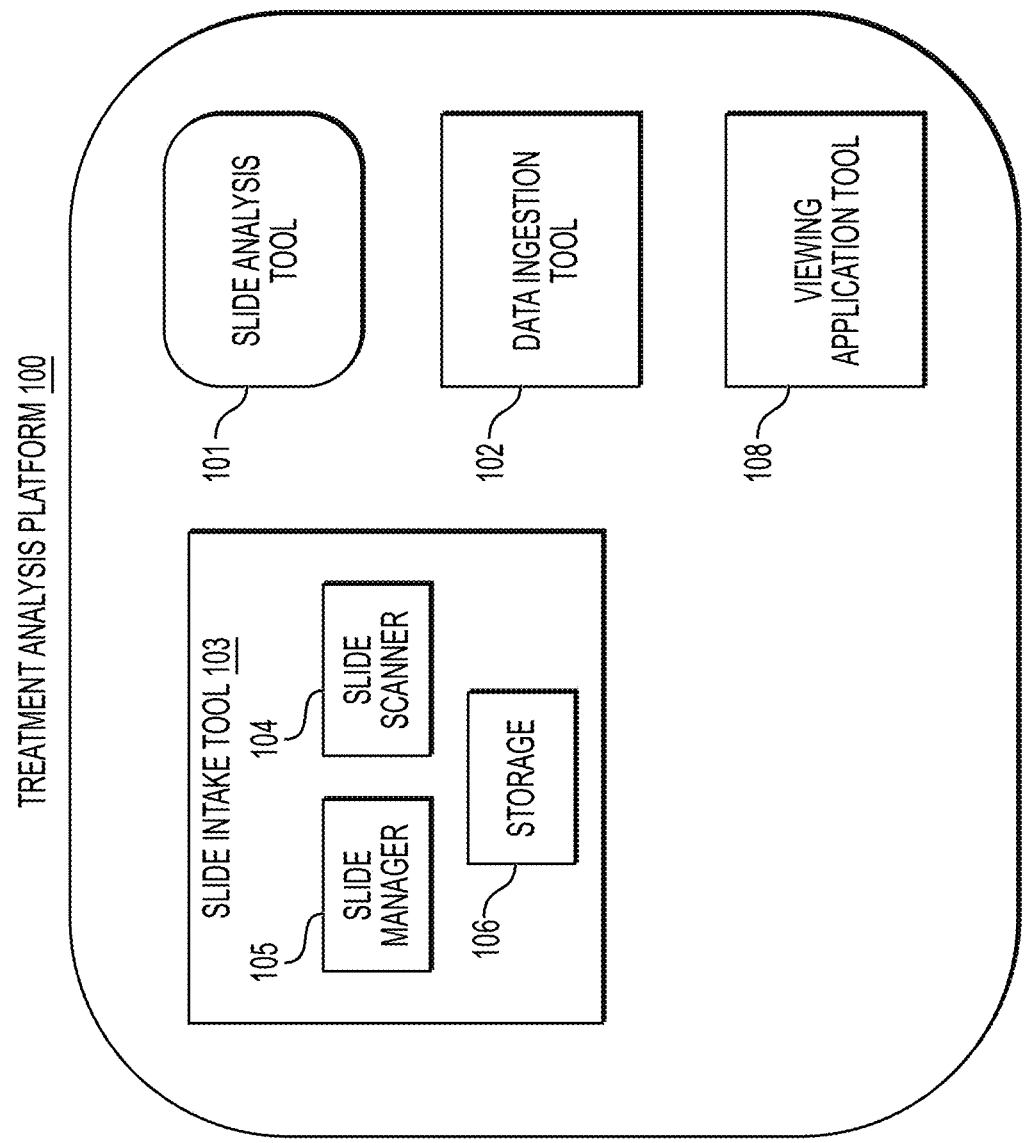
FIG. 1B illustrates an exemplary block diagram of the treatment analysis platform 100, according to an exemplary of the present disclosure.

FIG. 1B illustrates an exemplary block diagram of a treatment analysis platform 100 for determining specimen property or image property information pertaining to digital pathology image(s), using machine learning. The treatment analysis platform 100 may include a slide analysis tool 101, a data ingestion tool 102, a slide intake tool 103, a slide scanner 104, a slide manager 105, a storage 106, a laboratory information system 107 and a viewing application tool 108.

The slide analysis tool 101, as described below, refers to a process and system for determining diagnostic information pertaining to digital pathology image(s). Machine learning may be used to classify an image, according to an exemplary embodiment. The slide analysis tool 101 may also receive additional information associated with a pathology specimen, as described in the embodiments below.

The data ingestion tool 102 may facilitate a transfer of the digital pathology images to the various tools, modules, components, and devices that are used for classifying and processing the digital pathology images, according to an exemplary embodiment.

The slide intake tool 103 may scan pathology images and convert them into a digital form, according to an exemplary embodiment. The slides may be scanned with slide scanner 104, and the slide manager 105 may process the images on the slides into digitized pathology images and store the digitized images in storage 106.

The viewing application tool 108 may provide a user with a specimen property or image property information pertaining to digital pathology image(s), according to an exemplary embodiment. The information may be provided through various output interfaces (e.g., a screen, a monitor, a storage device and/or a web browser, etc.).

The slide analysis tool 101 and one or more of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the slide analysis tool 101, the data ingestion tool 102, the slide intake tool 103, the slide scanner 104, the slide manager 105, and the viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools and modules may be located on a device that may be connected to an electronic network such as the Internet or a cloud service provider, through one or more computers, servers and/or handheld mobile devices.

Figure 2A:
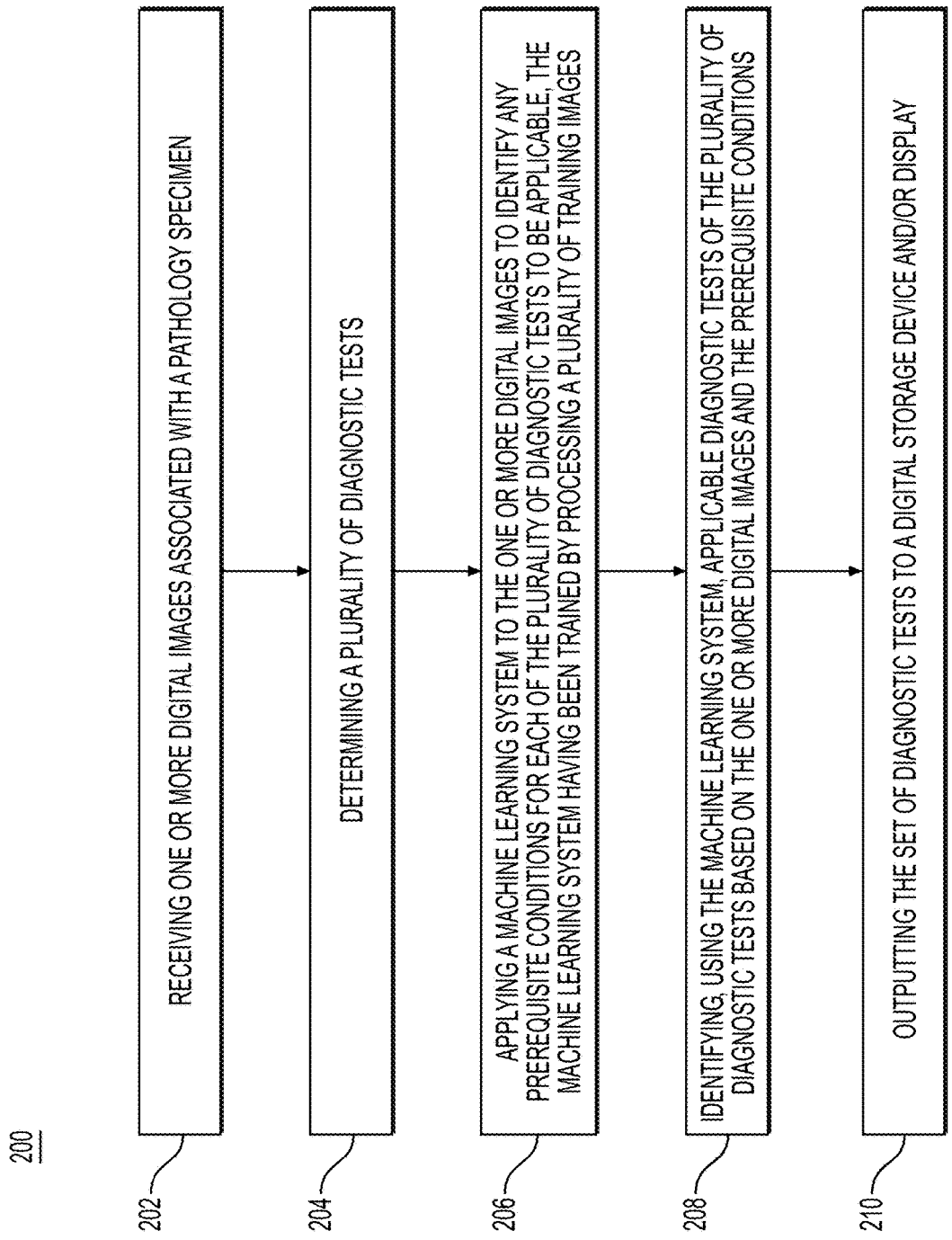
FIG. 2A is a flowchart illustrating an exemplary method for identifying diagnostic tests to apply to a pathology specimen, according to an exemplary embodiment of the present disclosure.

FIG. 2A illustrates a method for identifying a set of diagnostic tests for a pathology specimen, according to an exemplary embodiment of the present disclosure. For example, an exemplary method 200 (e.g., steps 202-210) may be performed by slide analysis tool 101 automatically or in response to a request from a user.

According to one embodiment, the exemplary method 200 for identifying a set of diagnostic tests to apply to a pathology specimen may include one or more of the following steps. In step 202, the method may include receiving one or more digital images associated with a pathology specimen (e.g., histology, cytology, etc.) into a digital storage device (e.g., hard drive, network drive, cloud storage, RAM, etc.).

Optionally, the method may include receiving additional information about a patient and/or a disease associated with the pathology specimen. This additional information may include, but is not limited to, patient demographics, prior medical history, additional clinical pathology and/or biochemical test results, radiology imaging, historical pathology specimen images, tumor size, cancer grade, stage of the cancer, information about the specimen (e.g., location of specimen sample, position in block, etc.) etc., into the digital storage device (e.g., hard drive, network drive, cloud storage, RAM, etc.).

Optionally, the method may include receiving additional testing information. This additional testing information may include, but is not limited to, availability of tests at local (nearby) medical facilities, test supplies, current clinical guidelines for testing, current regulatory indications for testing, average time for the result of one or more tests to be obtained (testing speed and turnaround time), current test pricing, available clinical trials, etc., into a digital storage device (e.g., hard drive, network drive, cloud storage, RAM, etc.).

Optionally, the method may also include receiving additional testing preferences information. This additional preferences information might include information about whether testing is covered by insurance (governmental healthcare, the patient's insurance, etc.), out-of-pocket payment after taking insurance to account, tests preferred by the doctor (lab, hospital), tests preferred by the patient (e.g., due to a religious practice, patient age, underlying medical condition, side effects, etc.), etc., into a digital storage device (e.g., hard drive, network drive, cloud storage, RAM, etc.).

In step 204, the method may include determining a plurality of diagnostic tests.

In step 206, the method may include applying a machine learning system to the one or more digital images to identify any prerequisite conditions for each of the plurality of diagnostic tests to be applicable, the machine learning system having been trained by processing a plurality of training images. Diagnostic tests may include, but are not limited to, molecular tissue tests (genomic sequencing, immunohistochemistry (IHC), fluorescence in situ hybridization (FISH), chromogenic in situ hybridization (CISH), in situ hybridization (ISH), genetic tests, special stains, algorithmic (computational, artificial intelligence, machine learning) testing, radiological testing, additional biopsies (specimens), lab tests (including biochemical and/or chemical pathology tests, such as blood, urine, sputum, etc.), etc., and output to a digital storage device (e.g., hard drive, electronic medical record, laboratory information system, networked drive, etc.) and/or user display (e.g., monitor, document, printed copy, etc.).

In step 208, the method may include identifying, using the machine learning model, applicable diagnostic tests of the plurality of diagnostic tests based on the one or more digital images and the prerequisite conditions. Scoring the diagnostic tests may indicate several representations of desirability. Examples include likely the likely patient benefit of the test, cost-effectiveness, efficiency of test results relative to benefit, preferred test ranking relative to benefit and/or to the availability of therapeutic agents or approaches with suggested therapeutic dosing and dosing schedules.

In step 210, the method may include outputting a ranked set of diagnostic tests to a digital storage device and/or display.

Optionally, the method may include inputting a scoring threshold and output one or more of, or only those tests that score above the threshold (including no tests if zero tests score above threshold).

Optionally, the method may include outputting one or more therapies, dosing, or dosing schedules that may be considered as a treatment strategy for the patient, or available clinical trials for the patient based on study inclusion and exclusion criteria and geographic proximity, based on the input information and/or additional suggested testing.

Optionally, the method may include displaying the ranked set of diagnostic tests to a user (e.g., referring clinician, testing laboratory, diagnostic company, therapeutics company, and/or patient). Test results may also be display using a customized interface, output document (e.g., PDF), printout, etc.

Figure 2B:
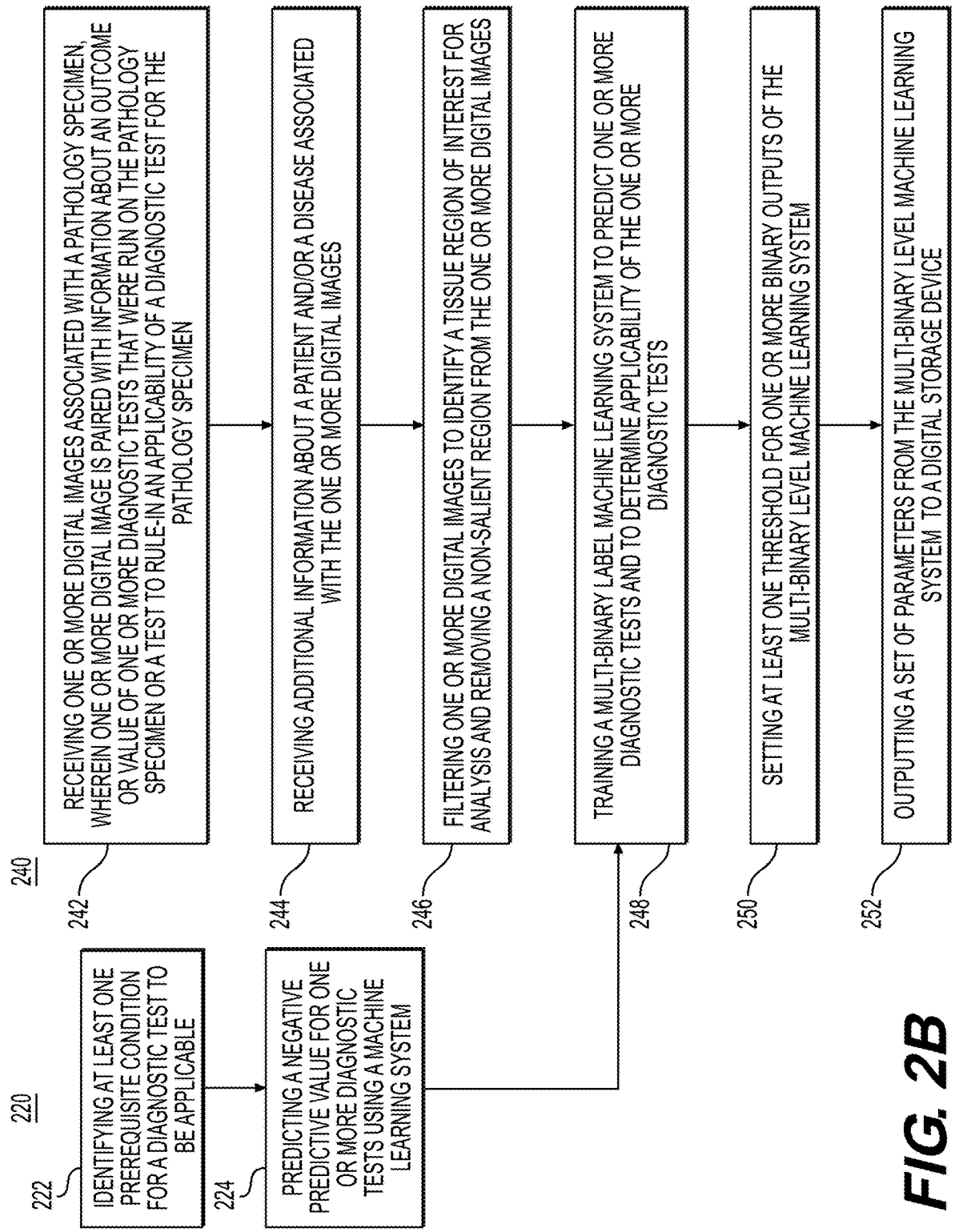
FIG. 2B is a flowchart illustrating an exemplary method for training a machine learning system for identifying relevant diagnostic tests, according to an exemplary embodiment of the present disclosure.

One or more exemplary embodiments may include one or more of the following three components:

Training a Machine Learning System for Identifying Test
   Applicability
Using the Trained System to Identify the Applicable Tests
Ranking the Applicable Tests based on Ancillary information Training a Machine Learning System for Identifying Test Applicability FIG. 2B is a flowchart illustrating an exemplary method for training a machine learning system for identifying test applicability, according to techniques presented herein. For example, exemplary methods 220 and 240 (e.g., steps 222-224 and steps 242-252) may be performed by slide analysis tool 101 automatically or in response to a request from a user.

According to one embodiment, the exemplary method 220 for training a machine learning system for identifying test applicability may include one or more of the following steps. In step 222, the method may include identifying at least prerequisite condition for a diagnostic test to be applicable. For example, some breast cancer recurrence tests (e.g., Oncotype DX) may require that a breast cancer patient may need to be estrogen receptor (ER) positive for the test to be applicable; if the computational assay identifies that a patient is likely not ER positive, then using Oncotype DX for the patient is ruled out.

In step 224, the method may include predicting a negative predictive value for one or more diagnostic tests using a machine learning system. For example, because genomic testing may be expensive and time consuming, determining that a patient does not have a mutation that is relevant for receiving a specific drug may indicate that performing the genomic test will not provide added value. If the system cannot rule-out the presence of the mutation, then genomic testing for the presence of that mutation might be a valid test to conduct. Another example is when immunohistochemical and/or genomic testing may be required in a population manner (e.g., NTRK fusion genes or microsatellite instability assessment in metastatic cancer patients) but the prevalence of the biomarker is low in the population. If the system cannot rule out the presence of the immunohistochemical and/or genomic feature, then the immunohistochemical and/or genomic test may be performed.

Method 240 is a flowchart for training the machine learning system, according to an exemplary embodiment. For example, an exemplary method 240 (e.g., steps 242-252) may be performed by slide analysis tool 101 automatically or in response to a request from a user. In step 242, the method may include receiving one or more digital images associated with a pathology specimen (e.g., histology, cytology, etc.) from a patient, wherein one or more digital image is paired with information about the outcome and/or value of one or more diagnostic tests that was done or test to rule-in the applicability of a diagnostic test, into a digital storage device (e.g., hard drive, network drive, cloud storage, RAM, etc.).

In step 244, the method may include receiving additional information about a patient and/or a disease associated with the one or more digital images. This additional information may include, but is not limited to, patient demographics, prior medical history, additional test results, radiology imaging, historical pathology specimen images, information about the specimen (e.g., location of specimen sample, position in block, etc.) etc., received into a digital storage device (e.g., hard drive, network drive, cloud storage, RAM, etc.).

In step 246, the method may include filtering one or more digital images to identify a tissue region of interest for analysis, and removing a non-salient region from the one or more digital images, the non-salient region being e.g. a background and/or anything not identified as a tissue region of interest. The region(s) of interest may be identified based on, at least in part, the additional information about the patient and/or disease. Region of interest/salient region determination may be performed using techniques discussed in U.S. application Ser. No. 17/313,617, which is incorporated herein by reference. Filtering the one or more images may be done with hand-annotations or using a region detector to identify salient regions (e.g., invasive tumor and/or invasive tumor stroma).

In step 248, the method may include training a multi-binary machine learning system to predict one or more diagnostic tests and whether the one or more diagnostic tests and to determine applicability of the one or more diagnostic tests. If a test was not done it is treated as missing data for a patient and not used to update the parameters of the machine learning system. If available, the additional patient data (medical history, existing results, etc.) may be input into the machine learning system to provide additional information (e.g., this may be done with neural network based methods by transforming this information into a vector and then using conditional batch normalization to regulate processing of the images). Numerous machine learning systems may be trained to do this by applying them to the image pixels for samples from each patient, including but not limited to:

a. Multi-layer perceptron (MLP)
   b. Convolutional neural network (CNN)
   c. Graph neural network
   d. Support vector machine (SVM)
   e. Random forest In step 250, the method may include setting at least one threshold for the one or more binary outputs of the machine learning system. For outputs corresponding to prerequisite conditions for a diagnostic test, the at least one threshold may be set to optimize for the detection of that prerequisite condition (e.g., presence of a biomarker that makes a diagnostic test applicable). For outputs corresponding to individual tests, the threshold may be set to optimize for the NPV to rule-out the applicability of that diagnostic test.

In steps 252, the method may include outputting a set of parameters from the multi-binary level machine learning system to a digital storage device (e.g., hard drive, network drive, cloud storage, RAM, etc.). The set of parameters may include the at least one threshold, and other data that tunes the machine learning system.

Using the Trained System to Identify the Applicable Tests

Figure 2C:
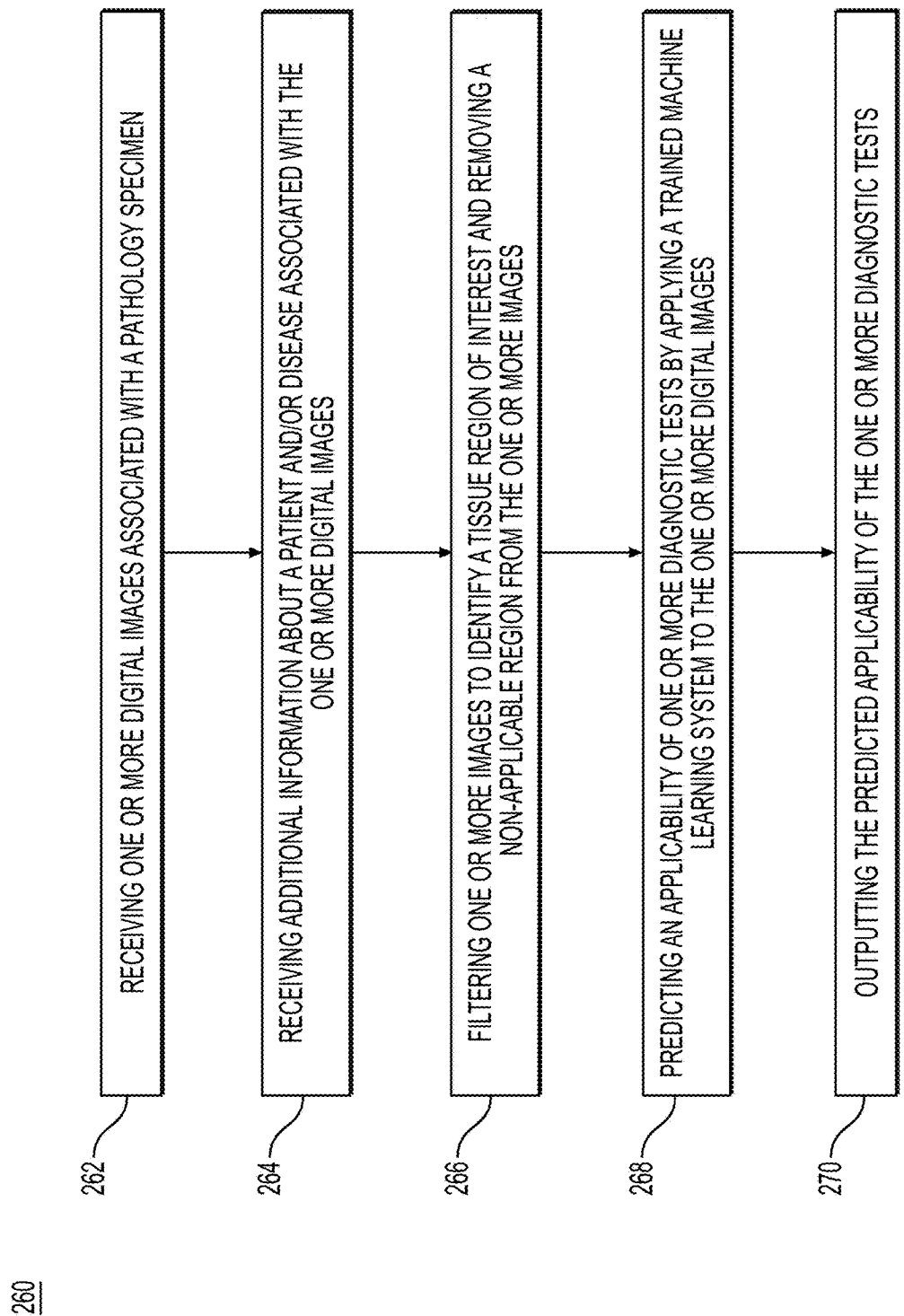
FIG. 2C is a flowchart illustrating an exemplary method for training the machine learning system, according to an exemplary embodiment of the present disclosure.

FIG. 2C is a flowchart for using the trained machine learning system for a patient, according to an exemplary method disclosed herein. After the machine learning system has been trained for determining applicable diagnostic tests, a user may apply the system to a patient. For example, an exemplary method 260 (e.g., steps 262-270) may be performed by slide analysis tool 101 automatically or in response to a request from a user. In step 262, the method may include receiving one or more digital images associated with a pathology specimen (e.g., histology, cytology, IHC, etc.) into a digital storage device (e.g., hard drive, network drive, cloud storage, RAM, etc.).

In step 264, the method may include receiving additional information about a patient and/or a disease associate with the one or more digital images. This additional information may include, but is not limited to, patient demographics, prior medical history, additional test results, radiology imaging, historical pathology specimen images, information about the specimen (e.g., location of specimen sample, position in block, etc.), into a digital storage device (e.g., hard drive, network drive, cloud storage, RAM, etc.).

In step 266, the method may include filtering one or more images to identify a tissue region of interest and removing a non-applicable region from the one or more images. Filtering may be done with hand-annotations or using a region detector to identify salient regions (e.g., invasive tumor and/or invasive tumor stroma).

In step 268, the method may include predicting an applicability of one or more diagnostic tests by applying a trained machine learning system to the one or more digital images.

In step 270, the method may include outputting the predicted applicability of the one or more diagnostic tests to a digital storage device (e.g., hard drive, network drive, cloud storage, RAM, etc.).

Ranking the Applicable Tests based on Ancillary information

FIG. 2D is a flowchart illustrating an exemplary method for ranking applicable diagnostic tests for a pathology specimen, according to techniques presented herein. After identifying the tests that are applicable, an optional step is to rank the applicable tests based on patient and clinician preferences, test availability, test availability, test costs, test speed, etc. For example, the exemplary method 280 (e.g., steps 282-290) may be performed by slide analysis tool 101 automatically or in response to a request from a user. In step 282, the method may include applying a trained machine learning system to identify a list of one or more applicable diagnostic tests for a pathology specimen, which produces an N-dimensional binary vector "y", where one or more elements corresponds to the applicability of an individual test.

In step 284, the method may include receiving additional testing and preferences information about the pathology specimen. Additional testing information may include, but is not limited to, availability of tests at local (nearby) medical facilities, test supplies, current clinical guidelines for testing, current regulatory indications for testing, average time for the result of one or more tests to be obtained (testing speeds), current test pricing, etc., into a digital storage device (e.g., hard drive, network drive, cloud storage, RAM, etc.). Additional preferences information might include information about which testing is covered by insurance (governmental healthcare, the patient's insurance, etc.), out-of-pocket payment after taking insurance to account, tests preferred by the doctor (lab, hospital), tests preferred by the patient (e.g., due to a religious practice, patient age, underlying medical condition, side effects, etc.), etc., into a digital storage device (e.g., hard drive, network drive, cloud storage, RAM, etc.).

In step 286, the method may include scoring one or more tests to produce an N-dimensional vector "s" of scores. There are numerous non-limiting ways this may be done:
a. Using only applicability and availability:
   i. Set s=y. For any or all tests that are predicted to be applicable, if the test is not available, set the corresponding element of s for that test to 0.
b. Using applicability, availability, and speed:
   i. Set s=y. For any or all tests that are predicted to be applicable, if the test is not available set the corresponding element of s for that test to 0, otherwise set the corresponding element of s to be inversely proportional to the speed such that faster tests will have larger scores.
c. Using applicability, availability, speed, and out-of-pocket patient cost:
   i. Set s=y. For any or all tests that are predicted to be applicable, if the test is not available set the corresponding element of s for that test to 0, otherwise set the corresponding element of s to be a weighted sum based on the user's preferences, where the first term in the sum is inversely proportional to the speed such that faster tests will have larger scores and the second term in the sum is inversely proportional to the cost of the test to the patient minus insurance coverage.
d. Using applicability, availability, speed, out-of-pocket patient cost, and patient preferences:
   i. Set s=y. For any or all tests that are predicted to be applicable, if the test is not available or if the test is one the patient cannot have (e.g., due to religious practices, age, discomfort, etc.) set the corresponding element of s for that test to 0, otherwise set the corresponding element of s to be a weighted sum based on the user's preferences, where the first term in the sum is inversely proportional to the speed such that faster tests will have larger scores and the second term in the sum is inversely proportional to the cost of the test to the patient minus insurance coverage.

In step 288, the method may include sorting the N-dimensional vector s such that higher scoring tests are preferred, which may involve sorting tests within the vector by test score.

Optionally, the method may include inputting a scoring threshold and outputting one or more of, or perhaps only those tests that score above the threshold (including no tests, if zero tests score above threshold).

Optionally, the method may also include outputting one or more therapies that may be suitable for the patient based on the input information in steps 282-288 and/or additional suggested testing.

In step 290, the method may include displaying test results to the user (e.g., referring clinician, testing laboratory, diagnostics company, therapeutics company and/or patient) using a customized interface, output document (e.g., PDF), printout, etc.

Figure 3:
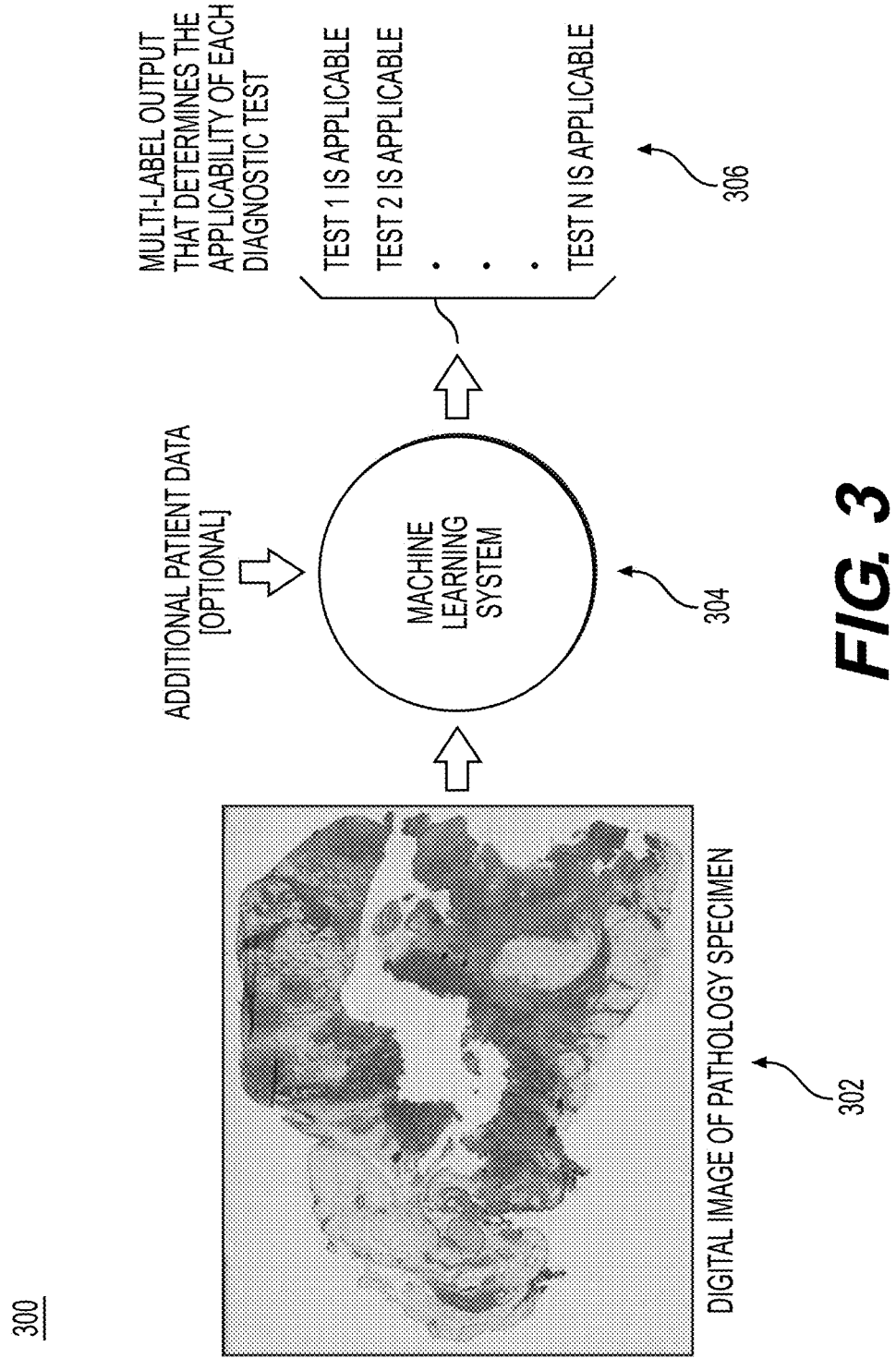
FIG. 3 is an exemplary workflow for determining test applicability, according to an exemplary embodiment of the present disclosure.

FIG. 3 is an exemplary workflow 300 of determining test applicability, according to techniques presented herein. FIG. 3 is a depiction of the system running on the image data from a patient to determine the applicability of N different diagnostic tests (before ranking), where the system outputs a 1 if the test is applicable and a 0 if it is not applicable.

In step 302, the workflow may include inputting a digital image of a pathology specimen. The pathology specimen and any available additional patient data may be input into a machine learning system in step 304.

In step 306, the workflow may include a multi-label output that determines the applicability of each diagnostic test.

Exemplary Embodiment: Ordering a Genomic, IHC, or ISH/FISH Test, Even Though Patient has Low Pre-Test Likelihood of a Certain Mutation or Antigen Genomic testing may be expensive, may not be available at all centers, may impose an additional cost, and may take significant time. Techniques presented herein may be used to determine when a genomic test is likely to provide diagnostic value, so that unneeded testing is avoided. One or more exemplary embodiments may be used to determine when an IHC, ISH/FISH test is applicable.

Training a Machine Learning System for Identifying Genomic, IHC, or ISH/FISH Test Applicability The steps for training the machine learning system may include:
1. Receive one or more digital images of pathology specimens (e.g., histology, cytology, etc.) from patients into a digital storage device (e.g., hard drive, network drive, cloud storage, RAM, etc.). For each patient, one or more images may be paired with information about the outcome of the genomic test (e.g., the presence/absence of oncogenic mutations/fusions for a list of genes), IHC tests, and/or ISH/FISH tests.
2. Optionally, receive additional patient information about each patient and/or disease. This additional patient information may include, but is not limited to, patient demographics, prior medical history, additional test results, radiology imaging, historical pathology specimen images, information about the specimen (e.g., location of specimen sample, position in block, etc.) etc., into a digital storage device (e.g., hard drive, network drive, cloud storage, RAM, etc.).
3. Optionally, filter one or more images to identify a tissue region of interest that should be used, which may be done with hand-annotations or using a region detector to identify salient regions (e.g., invasive tumor and/or invasive tumor stroma). Remove non-salient regions from one or more images.
4. Train a multi-binary label machine learning system to predict the presence of one or more oncogenic gene mutations/fusions. If available, the additional patient data (medical history, existing results, etc.) may be input into the machine learning system to provide additional information (e.g., this may be done with neural network based methods by using a transforming this information into a vector and then using conditional batch normalization to regulate processing of the images). Numerous machine learning systems may be trained to do this by applying them to the image pixels for samples from one or more patients, including but not limited to:
   i. Multi-layer perceptron (MLP)
   ii. Convolutional neural network (CNN)
   iii. Graph neural network
   iv. Support vector machine (SVM)
   V. Random forest
5. Thresholds may be set for one or more binary outputs of the system to optimize for the definitive absence of a mutation/fusion of each oncogene.
6. Output the trained system's parameters to a digital storage device (e.g., hard drive, network drive, cloud storage, RAM, etc.)

Using the Trained System to Identify Whether Genomic, IHC, or ISH/FISH Testing May be Necessary
1. Receive digital images of pathology specimens from a patient (e.g., histology, cytology, etc.) into a digital storage device (e.g., hard drive, network drive, cloud storage, RAM, etc.).
2. Optionally, receive additional patient information about the patient and/or disease. This additional patient information may include, but is not limited to, patient demographics, prior medical history, additional test results, radiology imaging, historical pathology specimen images, information about the specimen (e.g., location of specimen sample, position in block, etc.) etc., into a digital storage device (e.g., hard drive, network drive, cloud storage, RAM, etc.).
3. Optionally, filter one or more images to identify a tissue region of interest that should be used, which may be done with hand-annotations or using a region detector to identify salient regions (e.g., invasive tumor and/or invasive tumor stroma). Remove non-salient regions from one or more images.
4. Run the trained machine learning system on the digital images from the patient, incorporating additional patient information if it is available to produce an N-dimensional vector of multi-label outputs corresponding to the definitive absence of mutation/fusion of each oncogene.
5. Output the predictions to a digital storage device (e.g., hard drive, network drive, cloud storage, RAM, etc.)
6. Optionally, notify the user of which oncogenes have been ruled out and recommend if genomic testing should be conducted.

Exemplary Embodiment: Ordering Multiparameter Gene Expression Tests for Breast Cancer, Such as MammaPrint, OncotypeDX, EndoPredict, PAM50 (Prosigna) or Breast Cancer Index The use of multiparameter gene expression tests to guide the treatment decisions for breast cancer has been increasing. These tests identify patients with a higher risk of breast cancer recurrence. Some tests used are MammaPrint, which is a 70 gene assay, and Oncotype DX, which is a 20 gene assay, that helps guide treatment decisions if chemotherapy may benefit a patient who has invasive breast cancer. The prerequisite for Oncotype DX test may be that the patient is ER positive, so ER negative patients might need to be excluded. Other tests to determine whether patients may require chemotherapy are EndoPredict (12 gene risk score), PAM50 (50 gene assay) and breast cancer index.

Training a Machine Learning System for Identifying the Applicability of a Multiparameter Gene Expression Test for Breast Cancer Patients The steps for training the machine learning system may include:
1. Receive a plurality of invasive primary breast tumor digital images of a pathology specimens (e.g., histology) from patients into a digital storage device (e.g., hard drive, network drive, cloud storage, RAM, etc.). For each patient, one or more images may be paired with information regarding if the patient was ER positive or negative and if positive also includes the Oncotype DX score.
2. Optionally, receive additional patient information about each patient and/or disease. This additional patient information may include, but is not limited to, patient demographics, prior medical history, additional test results, radiology imaging, historical pathology specimen images, information about the specimen (e.g., location of specimen sample, position in block, etc.) etc., into a digital storage device (e.g., hard drive, network drive, cloud storage, RAM, etc.).
3. Optionally, filter one or more images to identify a tissue region of interest that should be used, which may be done with hand-annotations or using a region detector to identify salient regions (e.g., invasive tumor and/or invasive tumor stroma). Remove non-salient regions from one or more images.
4. Train a multi-binary label machine learning system to predict if the patient is ER positive or ER negative and train it to predict the Oncotype DX score for ER positive patients, treating the Oncotype DX score as a missing value otherwise (e.g., it will not be used to update the parameters if missing). For other tests, train a multi-label machine learning system to predict patient's cancer recurrence risk score. If available, the additional patient data (medical history, existing results, etc.) may be input into the machine learning system to provide additional information (e.g., this may be done with neural network based methods by using a transforming this information into a vector and then using conditional batch normalization to regulate processing of the images). Numerous machine learning systems may be trained to do this by applying them to the image pixels for samples from each patient, including but not limited to:
  i. Multi-layer perceptron (MLP)
  ii. Convolutional neural network (CNN)
  iii. Graph neural network
  iv. Support vector machine (SVM)
  v. Random forest Thresholds may be set for one or more binary outputs of the system, such that if the patient is determined by the system to be ER negative, Oncotype DX is indicated as not applicable, and such that if the patient is determined to have a very low test score to indicate that conducting the multi-parameter breast cancer gene expression test will likely lead to a prediction of a low risk of recurrence.

Output the trained system's parameters to a digital storage device (e.g., hard drive, network drive, cloud storage, RAM, etc.)

Using the Trained System

After the system has been trained for determining the applicability of the multiparameter breast cancer gene expression test, the steps for using the trained system for a patient may include:
  1. Receive invasive primary breast tumor digital images of pathology specimens from a patient (e.g., histology) into a digital storage device (e.g., hard drive, network drive, cloud storage, RAM, etc.).
  2. Optionally, receive additional patient information about the patient and/or disease. This additional patient information may include, but is not limited to, patient demographics, prior medical history, additional test results, radiology imaging, historical pathology specimen images, information about the specimen (e.g., location of specimen sample, position in block, etc.) etc., into a digital storage device (e.g., hard drive, network drive, cloud storage, RAM, etc.).
  3. Optionally, filter one or more images to identify a tissue region of interest that should be used, which may be done with hand-annotations or using a region detector to identify salient regions (e.g., invasive tumor and/or invasive tumor stroma). Remove non-applicable regions from one or more images.
  4. Run the trained machine learning system on the digital images from the patient, incorporating additional patient information if it is available. If the system predicts that the patient is ER negative, indicate that Oncotype DX is not recommended. If the system predicts that the patient likely has a low multiparameter breast cancer gene expression test score, indicate this to the user and recommend that this test not be used.
  5. Output the predictions to a digital storage device (e.g., hard drive, network drive, cloud storage, RAM, etc.)

Exemplary Embodiment: Ordering Multiparameter Gene Expression Tests for Prostate Cancer, Such as Oncotype DX Genomic Prostate Score (GPS), or Prolaris OncotypeDX GPS (17 gene assay) and Prolaris (46 gene assay) tests assess the likelihood of aggressiveness of prostate cancer and help guide treatment decisions. The higher the GPS score or Prolaris risk score, the more likely the cancer is aggressive and may require immediate treatment such as surgery or radiation therapy. The steps for training the machine learning system may include:
  1. Receive a plurality of prostate tumor digital images of a pathology specimens (e.g., histology) from patients into a digital storage device (e.g., hard drive, network drive, cloud storage, RAM, etc.). For each patient, one or more images may be paired with gene expression test for prostate cancer.
  2. Optionally, receive additional patient information about each patient and/or disease. This additional patient information may include, but is not limited to, patient demographics, prior medical history, additional test results, radiology imaging, historical pathology specimen images, information about the specimen (e.g., location of specimen sample, position in block, etc.) etc., into a digital storage device (e.g., hard drive, network drive, cloud storage, RAM, etc.).
  3. Optionally, filter one or more images to identify a tissue region of interest that should be used, which may be done with hand-annotations or using a region detector to identify salient regions. Remove non-salient regions from one or more images.
  4. Train a multi-binary label machine learning system to predict the OncoTypeDX GPS score/Prolaris score. If available, the additional patient data (medical history, existing results, etc.) may be input into the machine learning system to provide additional information (e.g., this may be done with neural network based methods by using a transforming this information into a vector and then using conditional batch normalization to regulate processing of the images). Numerous machine learning systems may be trained to do this by applying them to the image pixels for samples from each patient, including but not limited to:
    i. Multi-layer perceptron (MLP)
    ii. Convolutional neural network (CNN)
    iii. Graph neural network
    iv. Support vector machine (SVM)
    V. Random forest
  5. Thresholds may be set for one or more binary outputs of the system, such that if the patient is determined to have a very low test score to indicate that conducting the multiparameter prostate cancer gene expression test will likely lead to a prediction of a less aggressive prostate cancer.
  6. Output the trained system's parameters to a digital storage device (e.g., hard drive, network drive, cloud storage, RAM, etc.)

Using the Trained System

After the system has been trained for determining the applicability of Oncotype DX, the steps for using the trained system for a patient may include:
  1. Receive invasive primary breast tumor digital images of pathology specimens from a patient (e.g., histology) into a digital storage device (e.g., hard drive, network drive, cloud storage, RAM, etc.).
  2. Optionally, receive additional patient information about the patient and/or disease. This additional patient information may include, but is not limited to, patient demographics, prior medical history, additional test results, radiology imaging, historical pathology specimen images, information about the specimen (e.g., location of specimen sample, position in block, etc.)

etc., into a digital storage device (e.g., hard drive, network drive, cloud storage, RAM, etc.).
3. Optionally, filter one or more images to identify a tissue region of interest that should be used, which may be done with hand-annotations or using a region detector to identify salient regions. Remove non-applicable regions from one or more images.
4. Run the trained machine learning system on the digital images from the patient, incorporating additional patient information if it is available. If the system predicts that the patient likely has a low Oncotype DX GPS score or Prolaris score, indicate this to the user and recommend that Oncotype DX GPS or Prolaris not be used.
5. Output the predictions to a digital storage device (e.g., hard drive, network drive, cloud storage, RAM, etc.)

Exemplary Embodiment: Ordering a Single/Multiplex Immunohistochemical (IHC), Fluorescence In Situ Hybridization (FISH) Tests Such as HER2, Mismatch Repair (MMR) Repair Proteins, PD-L1

For the treatment of cancer types at a given clinical stage, additional IHC and/or FISH analyses may be essential for therapy decision-making, however the frequency of the marker is low. This is exemplified by the need of tumor site agnostic testing of all or multiple metastatic cancer patients for the presence of NTRK1, NTRK2 and NTRK3 fusion genes as well as microsatellite instability for the use of specific therapeutic regimes (I.e. TRK inhibitors and immune-check point inhibitors, respectively). Likewise, the testing of non-small cell lung cancer patients for the presence of ALK, RET and ROS1 rearrangements may be required for the treatment of these patients in the metastatic setting.

Training a Machine Learning System for Identifying the Applicability of a Single/Multiplex Immunohistochemical (IHC), Fluorescence In Situ Hybridization (FISH) Tests The steps for training the machine learning system may include:
1. Receive a plurality of digital images of pathology specimens (e.g., histology, cytology, etc.) from patients into a digital storage device (e.g., hard drive, network drive, cloud storage, RAM, etc.). For each patient, one or more images may be paired with information about the outcome of the IHC/FISH test or related genomic test.
2. Optionally, receive additional patient information about each patient and/or disease. This additional patient information may include, but is not limited to, patient demographics, prior medical history, additional test results, radiology imaging, historical pathology specimen images, information about the specimen (e.g., location of specimen sample, position in block, etc.) etc., into a digital storage device (e.g., hard drive, network drive, cloud storage, RAM, etc.).
3. Optionally, filter one or more images to identify a tissue region of interest that should be used, which may be done with hand-annotations or using a region detector to identify salient regions (e.g., invasive tumor, invasive tumor stroma). Remove non-salient regions from one or more images.
4. Train a multi-binary label machine learning system to predict the presence of the IHC/FISH marker. If available, the additional patient data (medical history, existing results, etc.) may be input into the machine learning system to provide additional information (e.g., this may be done with neural network based methods by transforming this information into a vector and then using conditional batch normalization to regulate processing of the images). Numerous machine learning systems may be trained to do this by applying them to the image pixels for samples from each patient, including but not limited to:
   i. Multi-layer perceptron (MLP)
   ii. Convolutional neural network (CNN)
   iii. Graph neural network
   iv. Support vector machine (SVM)
   v. Random forest
5. Thresholds may be set for one or more binary outputs of the system to optimize for the definitive absence of a given IHC/FISH marker.
6. Output the trained system's parameters to a digital storage device (e.g., hard drive, network drive, cloud storage, RAM, etc.)

Using the Trained System

After the system has been trained for determining the applicability of a single/multiplex immunohistochemical (IHC) test, the steps for using the trained system for a patient may include:
1. Receive digital images of pathology specimens from a patient (e.g., histology, cytology, etc.) into a digital storage device (e.g., hard drive, network drive, cloud storage, RAM, etc.).
2. Optionally, receive additional patient information about the patient and/or disease. This additional patient information may include, but is not limited to, patient demographics, prior medical history, additional test results, radiology imaging, historical pathology specimen images, information about the specimen (e.g., location of specimen sample, position in block, etc.) etc., into a digital storage device (e.g., hard drive, network drive, cloud storage, RAM, etc.).
3. Optionally, filter one or more images to identify a tissue region of interest that should be used, which may be done with hand-annotations or using a region detector to identify salient regions (e.g., invasive tumor and/or invasive tumor stroma). Remove non-salient regions from one or more images.
4. Run the trained machine learning system on the one or more digital images from the patient, incorporating additional patient information if it is available to produce an N-dimensional vector of multi-label outputs corresponding to the definitive absence of a given IHC/FISH marker.
5. Output the predictions to a digital storage device (e.g., hard drive, network drive, cloud storage, RAM, etc.)
6. Optionally, notify the user of which IHC/FISH markers have been ruled out and recommend if the type of IHC/FISH should be conducted.

Exemplary Embodiment: Ordering a Multi-Gene Sequencing Panel, Such as Foundation One CDx or MSK IMPACT Multi-gene panel analysis of tumor and/or tumor-normal pairs have been shown to result in benefit for cancer patients, with studies demonstrating that in up to >10% of metastatic cancer patients, multi-gene sequencing assays may receive more appropriate therapies and/or be enrolled in clinical trials solely on the basis of the results of these molecular tests. For the vast majority of patients, however, the information provided by these assays is of limited or no current utility. In addition, these assays are relatively expensive, have a long turnaround time, and are available only in a limited number of institutions.

Training a Machine Learning System for Identifying the Applicability of a Multi-Gene Sequencing Panel The steps for training the machine learning system may include:
1. Receive a plurality of digital images of pathology specimens (e.g., histology, cytology, etc.) from patients into a digital storage device (e.g., hard drive, network drive, cloud storage, RAM, etc.). For each patient, one or more images may be paired with information about the outcome of the multi-gene sequencing assay.
2. Optionally, receive additional patient information about each patient and/or disease. This additional patient information may include, but is not limited to, patient demographics, prior medical history, additional test results, radiology imaging, historical pathology specimen images, information about the specimen (e.g., location of specimen sample, position in block, etc.) etc., into a digital storage device (e.g., hard drive, network drive, cloud storage, RAM, etc.).
3. Optionally, filter one or more images to identify a tissue region of interest that should be used, which may be done with hand-annotations or using a region detector to identify salient regions (e.g., invasive tumor and/or invasive tumor stroma). Remove non-salient regions from one or more images.
4. Train a multi-binary label machine learning system to predict the result of the multi-gene sequencing assay. If available, the additional patient data (medical history, existing results, etc.) may be input into the machine learning system to provide additional information (e.g., this may be done with neural network based methods by using a transforming this information into a vector and then using conditional batch normalization to regulate processing of the images). Numerous machine learning systems may be trained to do this by applying them to the image pixels for samples from each patient, including but not limited to:
    i. Multi-layer perceptron (MLP)
    ii. Convolutional neural network (CNN)
    iii. Graph neural network
    iv. Support vector machine (SVM)
    v. Random forest
5. Thresholds may be set for one or more binary outputs of the system to optimize for the definitive absence of a clinically relevant finding stemming from the multi-gene sequencing assay.
6. Output the trained system's parameters to a digital storage device (e.g., hard drive, network drive, cloud storage, RAM, etc.)

Using the Trained System

After the system has been trained for determining the applicability of a multi-gene sequencing panel, the steps for using the trained system for a patient may include:
1. Receive digital images of pathology specimens from a patient (e.g., histology, cytology, etc.) into a digital storage device (e.g., hard drive, network drive, cloud storage, RAM, etc.).
2. Optionally, receive additional patient information about the patient and/or disease. This additional patient information may include, but is not limited to, patient demographics, prior medical history, additional test results, radiology imaging, historical pathology specimen images, information about the specimen (e.g., location of specimen sample, position in block, etc.) etc., into a digital storage device (e.g., hard drive, network drive, cloud storage, RAM, etc.).
3. Optionally, filter one or more images to identify a tissue region of interest that should be used, which may be done with hand-annotations or using a region detector to identify salient regions (e.g., invasive tumor and/or invasive tumor stroma). Remove non-salient regions from one or more images.

Run the trained machine learning system on the digital images from the patient, incorporating additional patient information if it is available to produce an N-dimensional vector of multi-label outputs corresponding to the definitive absence of a clinically relevant result stemming from the multi-gene sequencing assay.

Output the predictions to a digital storage device (e.g., hard drive, network drive, cloud storage, RAM, etc.)

Optionally, notify the user of which genetic and genomic alterations have been ruled out and recommend if the multi-gene sequencing assay should be conducted.

Exemplary Embodiment: Ordering Assays to Prioritize Immuno-Oncology (IO) Therapies Immuno-therapies are reshaping the treatment landscape for patients with different cancer types. Tumor-specific (e.g. PD-L1 assessment in non-small cell lung cancer and metastatic triple-negative breast cancer), as well as cancer site agnostic (e.g. microsatellite instability (MSI) or mismatch repair deficiency (dMMR) and tumor mutation burden (TMB)) biomarkers for treatment decision-marking may now be required. Their assessment, however, often includes multiple modalities of assays (e.g. IHC, PCR and/or multi-gene sequencing assays), which are expensive, have a long turnaround time and need subsequent integration.

Furthermore new panels to better understand the composition of the tumor microenvironment as well as the immune characteristics of the patients are being developed. PanCancer IO 360 gene expression panel is a 770 target, multiplexed gene expression panel developed for characterization of expression patterns from the tumor, immune system, and stroma. It contains the Tumor Inflammation Signature (TIS), which includes 18 functional genes known to be associated with response to PD-1/PD-L1 inhibitors pathway blockade. PanCancer IO360 panel as well TIS have the potential in helping physicians with the treatment decisions for IO therapies.

Training a Machine Learning System for Identifying Assays to Help Prioritize Immune-Oncology Therapies The steps for training the machine learning system may include:
4. Receive a plurality of digital images of pathology specimens (e.g., histology, cytology, etc.) from patients into a digital storage device (e.g., hard drive, network drive, cloud storage, RAM, etc.). For each patient, one or more images may be paired with information about the specific biomarkers for immuno-therapy response (e.g. PD-L1 expression, Microsatellite Instability High/Deficient Mismatch Repair (MSI/dMMR), tumor mutational burden (TMB), PanCancer IO360 panel, TIS).
5. Optionally, receive additional patient information about each patient and/or disease. This additional patient information may include, but is not limited to, patient demographics, prior medical history, additional test results, radiology imaging, historical pathology specimen images, information about the specimen (e.g., location of specimen sample, position in block, etc.)

etc., into a digital storage device (e.g., hard drive, network drive, cloud storage, RAM, etc.).
6. Optionally, filter one or more images to identify a tissue region of interest that should be used, which may be done with hand-annotations or using a region detector to identify salient regions (e.g., invasive tumor and/or invasive tumor stroma). Remove non-salient regions from one or more images.
7. Train a multi-binary label machine learning system to predict the presence of one or more specific biomarkers for immuno-therapy response (e.g. PD-L1 expression, MSI/dMMR, TMB, PanCancer IO360 panel, TIS). If available, the additional patient data (medical history, existing results, etc.) may be input into the machine learning system to provide additional information (e.g., this may be done with neural network based methods by using a transforming this information into a vector and then using conditional batch normalization to regulate processing of the images). Numerous machine learning systems may be trained to do this by applying them to the image pixels for samples from each patient, including but not limited to:
   i. Multi-layer perceptron (MLP)
   ii. Convolutional neural network (CNN)
   iii. Graph neural network
   iv. Support vector machine (SVM)
   V. Random forest
8. Thresholds may be set for one or more binary outputs of the system to optimize for the definitive absence of a mutation/fusion of one or more specific biomarkers for immuno-therapy response (e.g. PD-L1 expression, MSI/dMMR, TMB, PanCancer IO360 panel, TIS).
9. Output the trained system's parameters to a digital storage device (e.g., hard drive, network drive, cloud storage, RAM, etc.)

Using the Trained System for Identifying Assays to Help Prioritize Immune-Oncology Therapies The steps for using the trained the machine learning system may include:
1. Receive digital images of pathology specimens from a patient (e.g., histology, cytology, etc.) into a digital storage device (e.g., hard drive, network drive, cloud storage, RAM, etc.).
2. Optionally, receive additional patient information about the patient and/or disease. This additional patient information may include, but is not limited to, patient demographics, prior medical history, additional test results, radiology imaging, historical pathology specimen images, information about the specimen (e.g., location of specimen sample, position in block, etc.) etc., into a digital storage device (e.g., hard drive, network drive, cloud storage, RAM, etc.).
3. Optionally, filter one or more images to identify a tissue region of interest that should be used, which may be done with hand-annotations or using a region detector to identify salient regions (e.g., invasive tumor and/or invasive tumor stroma). Remove non-applicable salient regions from one or more images.
4. Run the trained machine learning system on the digital images from the patient, incorporating additional patient information if it is available to produce an N-dimensional vector of multi-label outputs corresponding to the definitive absence of mutation/fusion of one or more specific biomarkers for immuno-therapy response (e.g. PD-L1 expression, MSI/dMMR, TMB, PanCancer IO 360 panel, TIS).
5. Output the predictions to a digital storage device (e.g., hard drive, network drive, cloud storage, RAM, etc.)
6. Optionally, notify the user of which specific biomarker for immuno-therapy response (e.g. PD-L1 expression, MSI/dMMR, TMB, PanCancer IO 360 panel, TIS) have been ruled out and recommend if IHC and/or genomic testing should be conducted.

Figure 4:
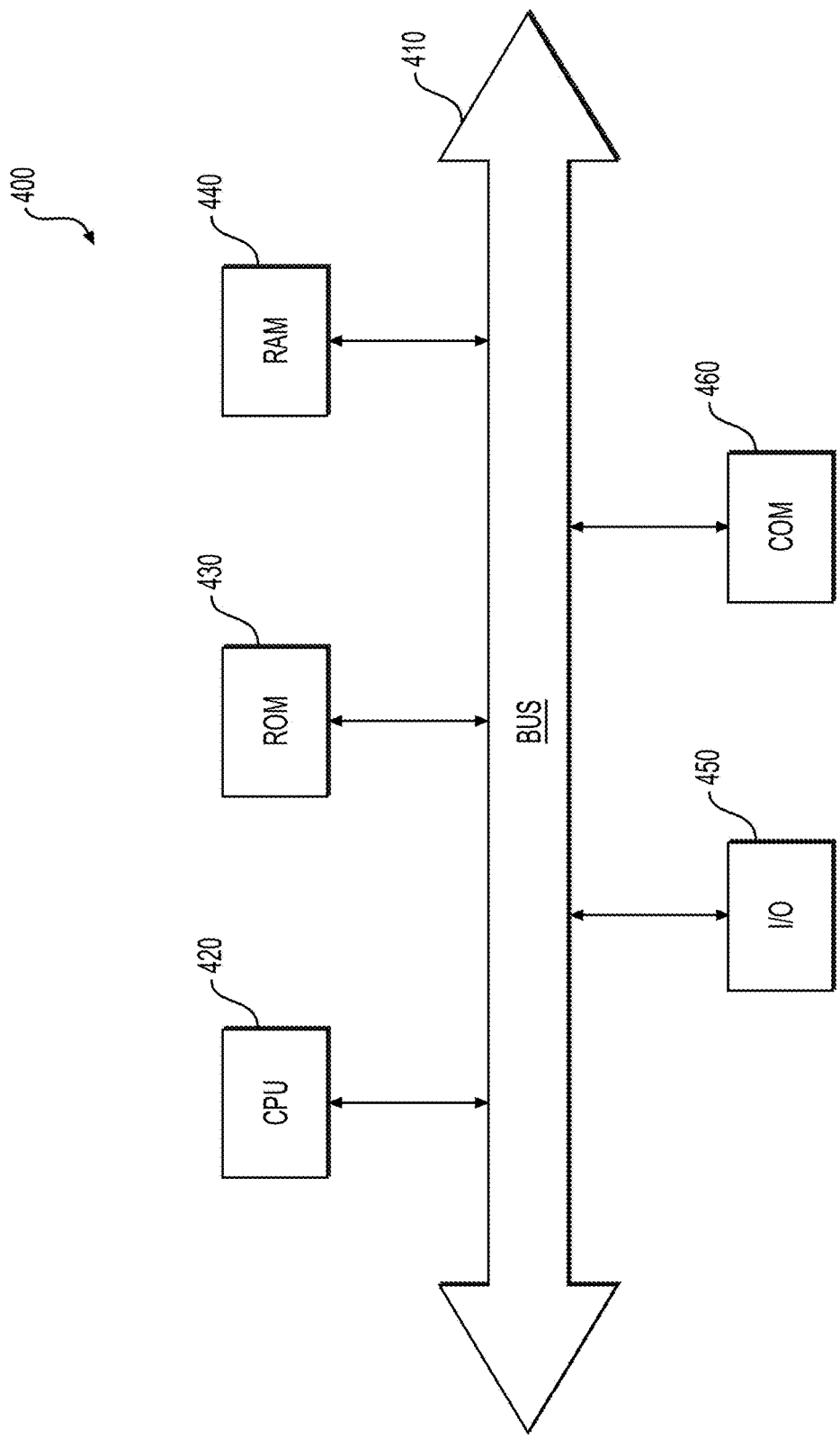
FIG. 4 depicts an example system that may execute techniques presented herein.

As shown in FIG. 4, device 400 may include a central processing unit (CPU) 420. CPU 420 may be any type of processor device including, for example, any type of special purpose or a general-purpose microprocessor device. As will be appreciated by persons skilled in the relevant art, CPU 420 also be may be a single processor in a multi-core/multiprocessor system, such system operating alone, or in a cluster of computing devices operating in a cluster or server farm. CPU 420 may be connected to a data communication infrastructure 410, for example a BUS, message queue, network, or multi-core message-passing scheme.

Device 400 may also include a main memory 440, for example, random access memory (RAM), and also may include a secondary memory 430. Secondary memory 430, e.g. a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 430 may include similar means for allowing computer programs of other instructions to be loaded into device 400. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 400.

Device 400 may also include a communications interface ("COM") 460. Communications interface 460 allows software and data to be transferred between device 400 and external devices. Communications interface 460 may include a modem, a network interface (such as an Ethernet card), a communications port, a PCMCIA slot and card, or the like. Software and data transferred via communications interface 460 may be in the form of signals, which may be electronic, electromagnetic, optical or other signals capable of being received by communications interface 460. These signals may be provided to communications interface 460 via a communications path of device 400, which may be implemented using, for example, wire or cable, fiber optics, a phone line, a cellular phone link, an RF link, or other communications channels.

The hardware elements, operating systems and programming languages of such equipment are conventional in nature, and it is presumed that those skilled in the art are adequately familiar therewith. Device 400 may also include input and output ports 450 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments may be apparent to those skilled in the art from consideration of the specification and practice of the invention disclosed herein. It is intended that the specification and examples be considered as exemplary only.

What is claimed is:

1. A computer-implemented method for training a machine-learning system to determine an applicability of a diagnostic test, the method comprising:
   receiving, by one or more processors, one or more digital images associated with a pathology specimen;
   receiving, by the one or more processors, a set of patient data associated with the one or more digital images;
   identifying, by the one or more processors, at least one tissue region of interest for analysis in the one or more digital images;
   determining and removing at least one non-applicable region from the one or more digital images, the at least one non-applicable region comprising at least one area not identified as a tissue region of interest;
   providing, by the one or more processors, the at least one tissue region of interest and the set of patient data to a machine-learning model as training data, wherein the machine-learning model is trained using the at least one tissue region of interest and the set of patient data to identify one or more applicable diagnostic tests;
   generating, by the one or more processors, at least one threshold for each of the one or more applicable diagnostic tests; and
   generating, by the one or more processors, a set of parameters for each of the one or more applicable diagnostic tests, the set of parameters including the at least one threshold.

2. The computer-implemented method of claim 1, wherein the set of patient data includes at least one of information about a patient, information about a disease, additional diagnostic test information, or additional test preference information.

3. The computer-implemented method of claim 1, further comprising:
   receiving, by the one or more processors, a set of specimen data associated with the pathology specimen, wherein the set of specimen data includes at least one of a location of a specimen sample or a position in a digital image block.

4. The computer-implemented method of claim 1, wherein identifying the at least one tissue region of interest for analysis in the one or more digital images is based, at least in part, on the set of patient data.

5. The computer-implemented method of claim 1, further comprising:
   identifying, by the one or more processors, at least one prerequisite condition for the one or more applicable diagnostic tests.

6. The computer-implemented method of claim 1, further comprising:
   scoring, by the one or more processors, the one or more applicable diagnostic tests including determining a weighted sum based on at least one predetermined preference.

7. The computer-implemented method of claim 1, wherein the machine-learning model is further trained to identify the one or more applicable diagnostic tests based on predicting a negative predictive value (NPV) for each of a plurality of diagnostic tests.

8. The computer-implemented method of claim 1, further comprising:
   transmitting, by the one or more processors, the one or more applicable diagnostic tests to at least one of a digital storage device or a display associated with a user device.

9. A system for training a machine-learning system to determine an applicability of a diagnostic test, the system comprising:
   at least one memory storing instructions; and
   at least one processor configured to execute the instructions to perform operations comprising:
      receiving, by one or more processors, one or more digital images associated with a pathology specimen;
      receiving, by the one or more processors, a set of patient data associated with the one or more digital images;
      identifying, by the one or more processors, at least one tissue region of interest for analysis in the one or more digital images;
      determining and removing at least one non-applicable region from the one or more digital images, the at least one non-applicable region comprising at least one area not identified as a tissue region of interest;
      providing, by the one or more processors, the at least one tissue region of interest and the set of patient data to a machine-learning model as training data, wherein the machine-learning model is trained using the at least one tissue region of interest and the set of patient data to identify one or more applicable diagnostic tests;
      generating, by the one or more processors, at least one threshold for each of the one or more applicable diagnostic tests; and
      generating, by the one or more processors, a set of parameters for each of the one or more applicable diagnostic tests, the set of parameters including the at least one threshold.

10. The system of claim 9, wherein the set of patient data includes at least one of information about a patient, information about a disease, additional diagnostic test information, or additional test preference information.

11. The system of claim 9, the operations further comprising:

receiving, by the one or more processors, a set of specimen data associated with the pathology specimen, wherein the set of specimen data includes at least one of a location of a specimen sample or a position in a digital image block.

12. The system of claim 9, wherein identifying the at least one tissue region of interest for analysis in the one or more digital images is based, at least in part, on the set of patient data.

13. The system of claim 9, the operations further comprising:
identifying, by the one or more processors, at least one prerequisite condition for the one or more applicable diagnostic tests.

14. The system of claim 9, the operations further comprising:
scoring, by the one or more processors, the one or more applicable diagnostic tests including determining a weighted sum based on at least one predetermined preference.

15. The system of claim 9, wherein the machine-learning model is further trained to identify the one or more applicable diagnostic tests based on predicting a negative predictive value (NPV) for each of a plurality of diagnostic tests.

16. The system of claim 9, the operations further comprising:
transmitting, by the one or more processors, the one or more applicable diagnostic tests to at least one of a digital storage device or a display associated with a user device.

17. A non-transitory computer readable medium storing instructions that, when executed by a processor, cause the processor to perform a method for training a machine-learning system to determine an applicability of a diagnostic test, the method comprising:
receiving, by one or more processors, one or more digital images associated with a pathology specimen;
receiving, by the one or more processors, a set of patient data associated with the one or more digital images;
identifying, by the one or more processors, at least one tissue region of interest for analysis in the one or more digital images;
determining and removing at least one non-applicable region from the one or more digital images, the at least one non-applicable region comprising at least one area not identified as a tissue region of interest;
providing, by the one or more processors, the at least one tissue region of interest and the set of patient data to a machine-learning model as training data, wherein the machine-learning model is trained using the at least one tissue region of interest and the set of patient data to identify one or more applicable diagnostic tests;
generating, by the one or more processors, at least one threshold for each of the one or more applicable diagnostic tests; and
generating, by the one or more processors, a set of parameters for each of the one or more applicable diagnostic tests, the set of parameters including the at least one threshold.

18. The non-transitory computer readable medium of claim 17, the method further comprising:
identifying, by the one or more processors, at least one prerequisite condition for the one or more applicable diagnostic tests.

19. The non-transitory computer readable medium of claim 17, the method further comprising:
scoring, by the one or more processors, the one or more applicable diagnostic tests including determining a weighted sum based on at least one predetermined preference.

20. The non-transitory computer readable medium of claim 17, wherein the machine-learning model is further trained to identify the one or more applicable diagnostic tests based on predicting a negative predictive value (NPV) for each of a plurality of diagnostic tests.

* * * * *